United States Patent
Chawla

(10) Patent No.: US 12,318,526 B2
(45) Date of Patent: Jun. 3, 2025

(54) SYRINGE-BASED MANUAL EXTRACORPOREAL BLOOD TREATMENT SYSTEMS AND METHODS EMPLOYING BATCH PROCESSING

(71) Applicant: Stavro Medical, Inc., Martinez, CA (US)

(72) Inventor: Lakhmir Singh Chawla, Martinez, CA (US)

(73) Assignee: Stavro Medical, Inc., Martinez, CA (US)

(*) Notice: Subject to any disclaimer, the term of this patent is extended or adjusted under 35 U.S.C. 154(b) by 478 days.

(21) Appl. No.: 17/743,167

(22) Filed: May 12, 2022

(65) Prior Publication Data

US 2022/0296797 A1   Sep. 22, 2022

Related U.S. Application Data

(63) Continuation of application No. PCT/US2020/064112, filed on Dec. 9, 2020.
(Continued)

(51) Int. Cl.
*A61M 1/36* (2006.01)
*A61M 1/14* (2006.01)
(Continued)

(52) U.S. Cl.
CPC ........ *A61M 1/3616* (2014.02); *A61M 1/1562* (2022.05); *A61M 1/1563* (2022.05);
(Continued)

(58) Field of Classification Search
CPC ............ A61M 1/30; A61M 1/34; A61M 1/36; A61M 39/10; A61M 1/1562;
(Continued)

(56) References Cited

U.S. PATENT DOCUMENTS

| 4,599,165 A | 7/1986 | Chevallet |
| 5,227,049 A | 7/1993 | Chevallet et al. |

(Continued)

FOREIGN PATENT DOCUMENTS

| DE | 19633657 C1 | 11/1997 |
| EP | 2720733 B1 | 9/2017 |

(Continued)

OTHER PUBLICATIONS

EP Appln. No. 20899971.4, Extended European Search Report, May 3, 2024, 9 pages.

(Continued)

*Primary Examiner* — John Kim
(74) *Attorney, Agent, or Firm* — Kilpatrick Townsend & Stockton LLP

(57) ABSTRACT

The disclosure provides a manual blood or body fluid treatment system comprising first and second reservoirs for holding a batch of blood from a patient and a filter for performing an extracorporeal treatment on blood passing therethrough by removing waste molecules and/or fluid. The first reservoir is constructed to be displaced vertically relative to the second reservoir and vice versa, such that a height difference between the first and second reservoirs causes blood or body fluid to flow between the reservoirs due to gravity.

12 Claims, 9 Drawing Sheets

Related U.S. Application Data

(60) Provisional application No. 63/057,129, filed on Jul. 27, 2020, provisional application No. 62/947,344, filed on Dec. 12, 2019.

(51) Int. Cl.
    *A61M 1/30* (2006.01)
    *A61M 1/34* (2006.01)
    *A61M 39/10* (2006.01)

(52) U.S. Cl.
    CPC ........ *A61M 1/1565* (2022.05); *A61M 1/1566* (2022.05); *A61M 1/302* (2014.02); *A61M 1/303* (2014.02); *A61M 1/3672* (2013.01); *A61M 39/10* (2013.01)

(58) Field of Classification Search
    CPC .............. A61M 1/1563; A61M 1/1565; A61M 1/1566; A61M 1/302; A61M 1/303; A61M 1/342; A61M 1/3604; A61M 1/3616; A61M 1/3672
    See application file for complete search history.

(56) References Cited

U.S. PATENT DOCUMENTS

| | | |
|---|---|---|
| 5,318,511 A | 6/1994 | Riquier et al. |
| 2004/0054320 A1 | 3/2004 | Kissinger et al. |
| 2005/0205476 A1 | 9/2005 | Chevallet et al. |
| 2011/0137224 A1* | 6/2011 | Ibragimov .............. A61M 1/34 604/4.01 |
| 2011/0178452 A1 | 7/2011 | Kopperschmidt |
| 2014/0074007 A1 | 3/2014 | Mcneil |
| 2014/0378893 A1 | 12/2014 | Tsyrulnyko |
| 2018/0117237 A1* | 5/2018 | Brugger .............. A61M 1/3646 |
| 2020/0147287 A1 | 5/2020 | Donato et al. |

FOREIGN PATENT DOCUMENTS

| | | |
|---|---|---|
| JP | 6145772 A | 3/1986 |
| WO | 9220383 A1 | 11/1992 |
| WO | 2017001357 A1 | 1/2017 |
| WO | 2021/119197 A1 | 6/2021 |
| WO | 2021/1119195 A1 | 6/2021 |

OTHER PUBLICATIONS

EP Application No. EP20898090.4, Extended European Search Report, Dec. 8, 2023, 7 pages.
Application No. PCT/US2020/064110, International Search Report and Written Opinion, Mailed On Apr. 13, 2021, 16 pages.
Application No. PCT/US2020/064112, International Search Report and Written Opinion, Mailed On Mar. 10, 2021, 15 pages.
U.S. Appl. No. 17/695,701, Non-Final Office Action, Oct. 11, 2024, 12 pages.
JP Application No. 2022-535621, Office Action, Sep. 3, 2024, 8 pages.

\* cited by examiner

SYRINGE-BASED MANUAL EXTRACORPOREAL BLOOD TREATMENT SYSTEMS AND METHODS EMPLOYING BATCH PROCESSING

CROSS-REFERENCES TO RELATED APPLICATIONS

The present application is a continuation of International Application No. PCT/US2020/064112, filed Dec. 9, 2020, which claims priority to U.S. Provisional Patent Application No. 62/947,344, filed Dec. 12, 2019, and 63/057,129, file Jul. 27, 2020, the contents all of which are incorporated by reference their entireties for all purposes.

BACKGROUND OF THE INVENTION

Field

The present disclosure relates generally to extracorporeal blood treatments, and more particularly, to manual extracorporeal blood treatment systems and methods employing batch processing.

BRIEF SUMMARY OF THE INVENTION

In one embodiment, the disclosure provides a manual blood treatment system comprising:
first and second reservoirs for holding a batch of blood from a patient;
a first conduit for conveying blood from a vascular access of the patient during a first stage and for returning treated blood to the vascular access during a third stage, the first conduit having only a single lumen;
a filter for performing, during a second stage, an extracorporeal treatment on blood passing therethrough by removing waste molecules and/or fluid; and
a first syringe coupled to the first conduit via a first valve between the vascular access and the first reservoir,
wherein fluid ports of the first and second reservoirs are connected to each other by a flow path through the filter such that the batch of blood can flow between the first and second reservoirs via the filter, and
the first reservoir is constructed to be displaced vertically relative to the second reservoir and vice versa, such that a height difference between the first and second reservoirs causes blood to flow between the reservoirs due to gravity.

In certain aspects, the first syringe is configured to: apply a vacuum pressure to the vascular access when the first valve is in a first orientation to withdraw a volume of blood from the patient via the first conduit, and apply a positive pressure when the first valve is in a second orientation to push the withdrawn volume of blood along the first conduit to the first reservoir.

In certain aspects, the system further comprises a second syringe coupled to a drain line from the filter via a second valve, wherein the second syringe is configured to apply a vacuum pressure to the filter when the second valve is in a first orientation, and apply a positive pressure to push effluent received from the filter along the drain line for disposal when the second valve is in a second orientation.

In certain aspect, the filter is constructed to provide a hemodialysis, hemofiltration, hemodiafiltration, hemoperfusion or a combination treatment to the blood flowing along the flow path through the filter.

In certain aspects, the system further comprises one or more additional valves disposed along the first conduit between the vascular access and the first valve or between the first valve and the first reservoir, wherein the first syringe is further configured to apply a vacuum pressure to a source of secondary fluid or drug connected to the one or more additional valves when the first valve is in the first orientation to withdraw a volume of secondary fluid or drug, and apply a positive pressure when the first valve is in the second orientation to push the withdrawn volume of secondary fluid or drug along the first conduit to the first reservoir.

In certain aspects, the secondary fluid or drug comprises at least one of replacement fluid, flushing fluid, intravenous fluid, anticoagulant, or anticoagulant reversal agent.

In another embodiment, the disclosure provides a manual blood treatment method comprising:
(a) using a first syringe coupled to a first conduit by a first valve in a first orientation, applying a vacuum to a vascular access of a patient to withdraw a first volume of blood from a patient;
(b) switching the first valve to a second orientation;
(c) with the first valve in the second orientation, applying a positive pressure using the first syringe to convey the first volume of blood to a first reservoir;
(d) changing respective heights of the first reservoir and a second reservoir, such that the first reservoir is higher than the second reservoir and such that blood in the first reservoir is conveyed to the second reservoir via a flowpath through a filter;
(e) after (d), changing respective heights of the first and second reservoirs such that the second reservoir is higher than the first reservoir and such that blood in the second reservoir is returned to the first reservoir via the flowpath through the filter;
(f) with the first valve in the second orientation, applying a vacuum using the first syringe to withdraw a second volume of blood from the first reservoir;
(g) switching the first valve to the first orientation; and
(h) with the first valve in the first orientation, applying a positive pressure using the first syringe to convey the second volume of blood into the patient via the vascular access.

In certain aspects, the method further comprises, during (d) and/or (e), using a second syringe coupled to a drain line of the filter by a second valve in a first orientation, applying a vacuum to the filter to withdraw effluent therefrom.

In certain aspects, the method further comprises switching the second valve to a second orientation and applying a positive pressure using the second syringe to convey the withdrawn effluent along the drain line away from the filter for disposal.

In certain aspects, steps (d) and (e) are repeated more than once to filter the same blood multiple times before proceeding to (f).

In certain aspects, steps (d) and (e) are effective to perform a hemodialysis, hemofiltration, hemodiafiltration, or hemoperfusion treatment on the blood flowing along the flow path through the filter.

In certain aspects, the second volume of blood is less than the first volume of blood.

In certain aspects, the method further comprises at least one of:
(S1) infusing a secondary fluid or drug to the first reservoir by:
(S1a) switching the first valve to the first orientation and a third valve, which couples a secondary fluid/drug source to the first conduit, to a first orientation;

(S1b) applying a vacuum to the first conduit to draw a volume of the secondary fluid or drug from the secondary fluid/drug source;
(S1c) switching the first valve to the second orientation; and
(S1d) with the first valve in the second orientation, applying a positive pressure using the first syringe to convey the volume of secondary fluid or drug to the first reservoir; or
(S2) infusing another secondary fluid or drug to the patient by:
(S2a) switching the first valve to the second orientation and a fourth valve, which couples another secondary fluid/drug source to the first conduit, to a first orientation;
(S2b) applying a vacuum to the first conduit to draw a volume of the another secondary fluid or drug from the another secondary fluid/drug source;
(S1c) switching the first valve to the first orientation; and
(S1d) with the first valve in the first orientation, applying a positive pressure using the first syringe to convey the volume of the another secondary fluid or drug to the patient via the vascular access.

These and other aspects, objects and embodiments will become more apparent when read with the detailed description and figures that follow.

BRIEF DESCRIPTION OF THE DRAWINGS

Embodiments will hereinafter be described with reference to the accompanying drawings, which have not necessarily been drawn to scale. Where applicable, some elements may be simplified or otherwise not illustrated in order to assist in the illustration and description of underlying features. Throughout the figures, like reference numerals denote like elements.

DETAILED DESCRIPTION OF THE INVENTION

Systems and methods according to the present disclosure employ batch processing of blood using manual actuation to convey blood and/or fluids to effect a desired extracorporeal blood treatment, for example, hemofiltration, hemodialysis, hemodiafiltration, or hemoperfusion. For example, a series of valves can allow a primary syringe to convey blood between a patient and one of a pair of blood reservoirs. The primary syringe can also be used to convey other fluids or drugs between the patient, the blood reservoirs, and respective fluid/drug sources. A blood volume (potentially with additional fluids and/or drugs) can be passed between the pair of blood reservoirs via a filter pathway interconnecting the reservoirs. Gravity can be used to convey the blood volume between reservoirs, e.g., by manually raising one of the reservoirs with the blood volume therein higher than the other. A secondary syringe can be used to apply a vacuum pressure to the filter to withdraw effluent from the blood volume as it passes along the filter pathway. Although the present disclosure uses "blood" as an exemplary body fluid, those of skill in the art will recognize that the systems and methods of the present disclosure are also useful for other body fluids such as blood, lymph, ascites, abdominal fluid, pleural fluid, organ fluid, spinal fluid, intestinal fluid or water. Similarly, although "vascular access" is an exemplary embodiment, a skilled artisan will recognize that abdominal access is needed for ascites, spinal canal access is needed for spinal fluid, and lymphatic access is need for lymph.

Since the disclosed embodiments can operate with a modest vascular access (e.g., a single lumen conduit or needle of relatively small size, for example, a catheter smaller than 7 French or a needle smaller than 17 gauge (e.g., smaller than either 7 French, such as 6, 5, 4, or 3 French or 17 gauge such as 16, 15, 14, 13, 12, 11, or 10 gauge), renal replacement therapies (RRT) may be more feasible and safer in austere conditions than conventional systems that require a peritoneal catheter or a double-lumen catheter, the placement of which can be challenging as they require technical expertise. Moreover, since the disclosed embodiments rely on manual actuation, they can be used in scenarios and environments where electrical power is unavailable or unreliable, unlike conventional dialysis machines. Thus, the disclosed embodiments may improve the availability of RRT for patients with acute kidney failure (AKI) and mitigate otherwise preventable deaths. Embodiments of the disclosed subject matter may exhibit additional or different advantages or features beyond those specifically delineated above.

Figure 1:
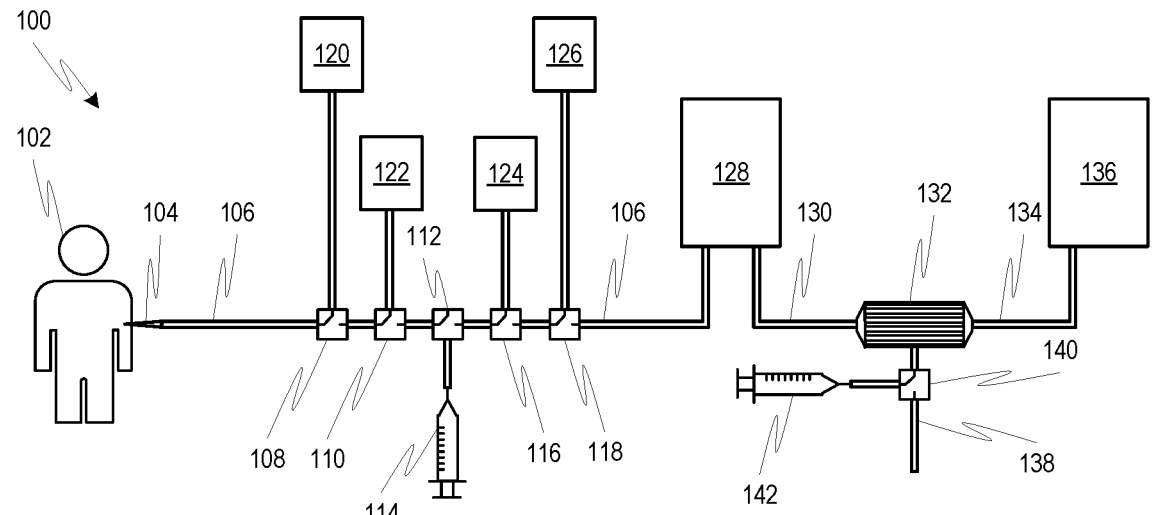
FIG. 1 is a simplified schematic diagram of a generalized manually-operated blood treatment system employing batch processing, according to one or more embodiments of the disclosed subject matter.

FIG. 1 illustrates aspects of a generalized manually-operated blood treatment system 100 that employs batch processing. The system 100 can have a vascular access 104 coupled to a single-lumen I/O conduit 106 to provide blood to/from patient 102. The vascular access 104 can comprise a needle, catheter, or other any other device for connecting to the patient vascular system known in the art. For example, the vascular access 104 can be a catheter or needle of either 2-11 French such as 2, 3, 4, 5, 6, 7, 8, 9, 10, or 11 French or 10-23 gauge such as 10, 11, 12, 13, 14, 15, 16, 17, 18, 19, 20, 21, 22, or 23 gauge.

A first fluid source 120 (e.g., 5% dextrose in sodium chloride, of D5-NS, or other hemofiltration fluid) can be connected to the conduit 106 via a respective supply line and valve 108. A first drug source 122 (e.g., anticoagulant, such as, but not limited to heparin, citrate-based anticoagulant, nafamostat, or epoprostenol) can be connected to the conduit 106 via a respective supply line and valve 110. A second drug source 124 (e.g., anticoagulant reversal agent (ARA), such as, but not limited to protamine and calcium) can be connected to the conduit 106 via a respective supply line and valve 116. A second fluid source 126 (e.g., Ringer's lactate solution or Hartmann's solution) can be connected to the conduit 106 via a respective supply line and valve 118. A primary syringe 114 (e.g., a 50-cc syringe) can be connected to the conduit 106 via a respective supply line and valve 112.

The valve 112 may be arranged along the flowpath of conduit 106 between the valve 110 for the first drug source 122 and the valve 116 for the second drug source 124. The valves 110, 116 for the drug sources 122, 124 may be arranged along the flowpath of conduit 106 between the valve 108 for the first fluid source 120 and the valve 118 for the second fluid source 126. For example, each of the valves 108, 110, 112, 116, and 118 may be a manually-actuated multi-position valve, such as a 3-way stopcock.

An end of conduit 106 opposite vascular access 104 can be connected to a fluid port of a first blood reservoir 128 (e.g., intravenous fluid (IV) or blood bag). Another fluid port of the first blood reservoir 128 can be connected to a first fluid port of a filtration device 132 (e.g., hemofilter) by a first fluid conduit 130 (e.g., IV tubing). A second blood reservoir 136 (e.g., IV or blood bag) can be connected to a second fluid port of the filtration device 132 by a second fluid conduit 134 (e.g., IV tubing). Each of the blood reservoirs 128, 136 may be displaced relative to each other (e.g., by moving the reservoir to a different attachment point on an IV pole), so as to provide a height difference that drives fluid flow therebetween and thus through filtration device 132.

An outlet port of the filtration device 132 can be coupled to a drain line 138. A secondary syringe 142 (e.g., a 50-cc syringe) can be connected to the drain line 138 via a respective supply line and valve 140. For example, valve 140 may also be a manually-actuated multi-position valve, such as a 3-way stopcock. The filtration device 132 can include a membrane therein that separates a flowpath for the blood from a waste volume coupled to drain line 138 via the outlet port of the filtration device 132. Secondary syringe 142 can apply a vacuum pressure to the outlet port that causes effluent to pass across the membrane from the flowing blood and into the drain line 138.

Figure 2A:
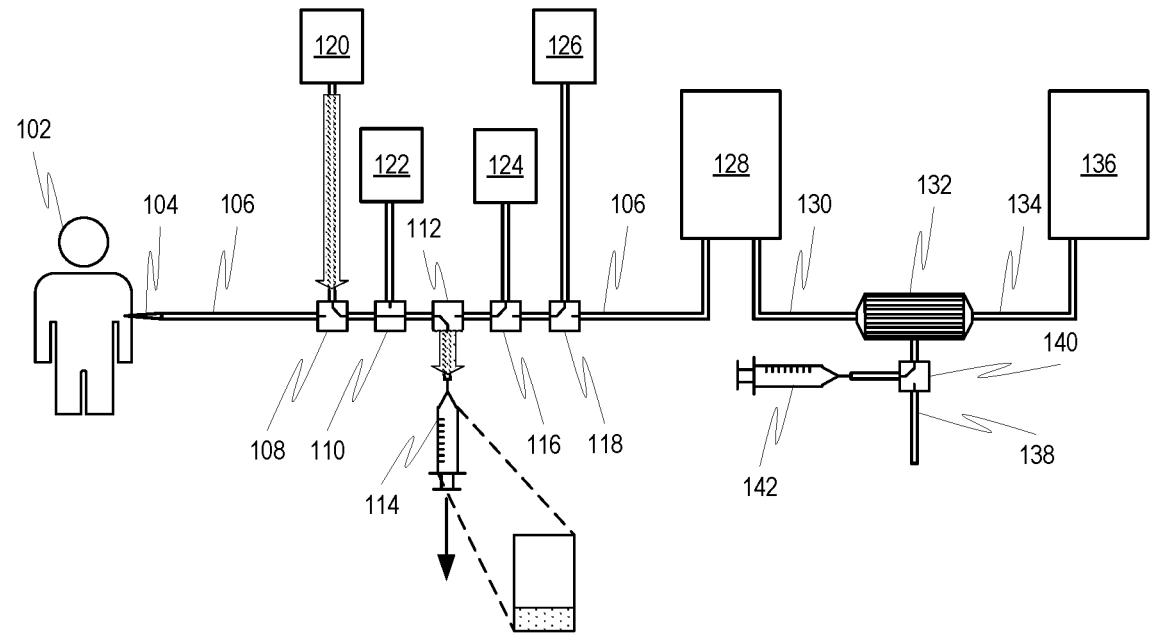
FIGS. 2A-2P are simplified schematic diagrams of the system of FIG. 1 during various stages of processing to provide hemofiltration of blood.
Figure 2B:
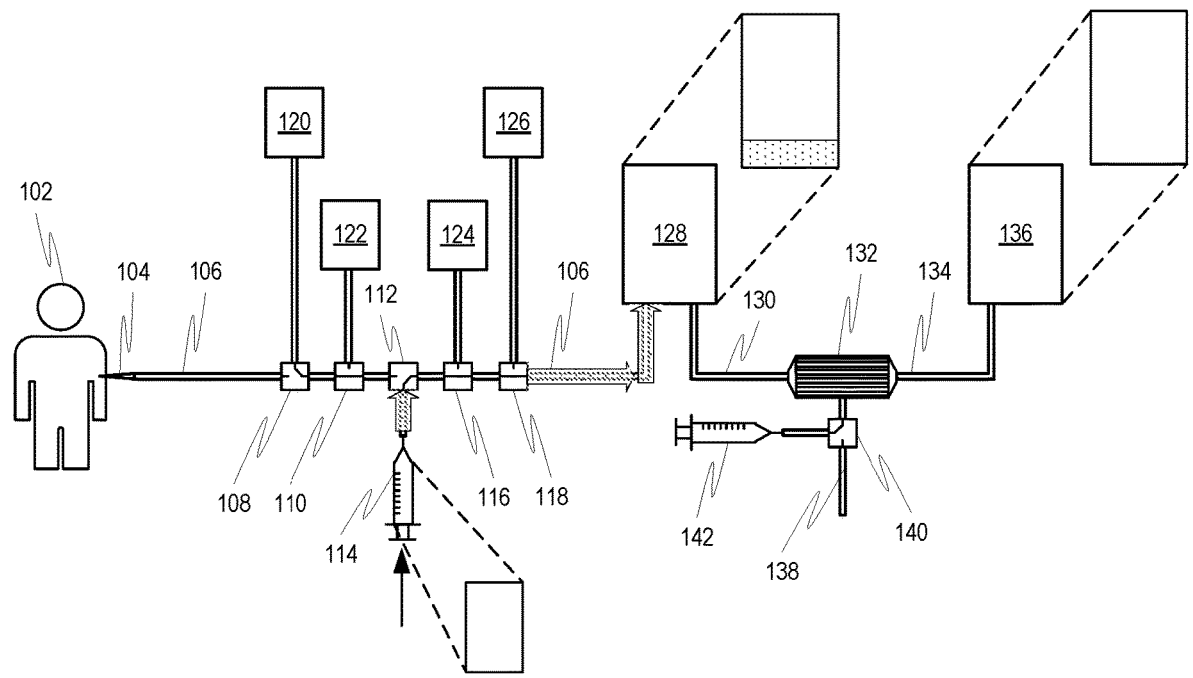

By appropriate actuation of the primary syringe 114 and control of valves 108, 110, 112, 116, and 118, body fluids, blood, fluids, and/or drugs can be sequentially introduced into the primary reservoir 128 in preparation for processing by filtration device 132. For example, FIG. 2A shows a first stage of providing a volume of first fluid from source 120 to reservoir 128. In particular, valves 108-112 are adjusted such that only source 120 is fluidically connected to primary syringe 114, whereby withdraw of the plunger of syringe 114 applies a vacuum pressure that draws first fluid from source 120 into the barrel of syringe 114. When a sufficient volume of first fluid has been transferred into the primary syringe 114, the system can be adjusted to the configuration of FIG. 2B, which shows a second stage of providing the volume of first fluid to reservoir 128. In particular, valves 112, 116, and 118 are adjusted such that only first blood reservoir 128 is fluidically connected to primary syringe 114, whereby depressing the plunger of syringe 114 applies a positive pressure that pushes first fluid from the syringe barrel into the first blood reservoir 128.

Figure 2C:
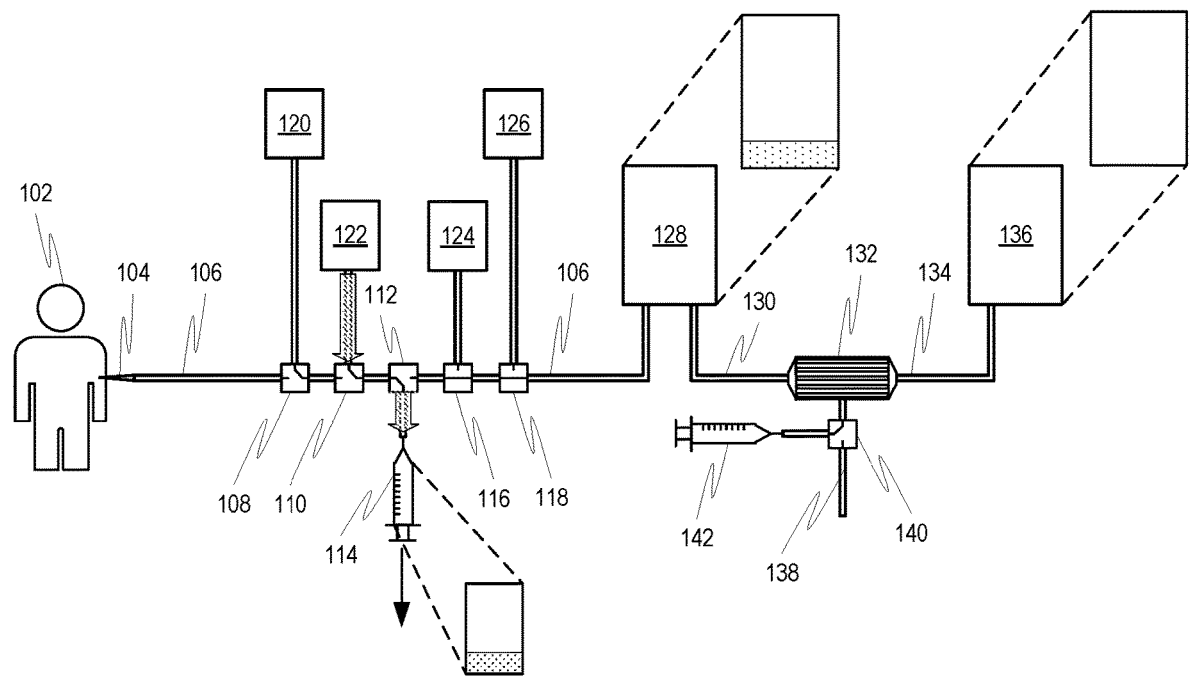
Figure 2D:
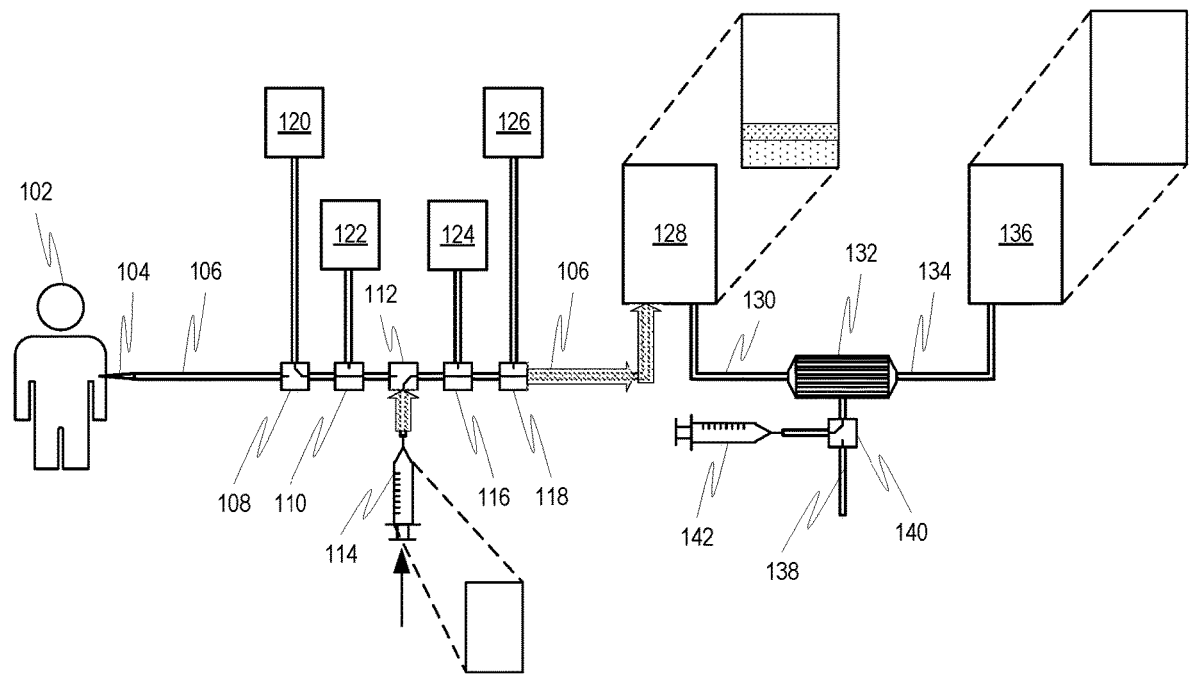

After the first fluid, a volume of first drug can be added. For example, FIG. 2C shows a first stage of providing a volume of first drug from source 122 to reservoir 128. In particular, valves 110-112 are adjusted such that only source 122 is fluidically connected to primary syringe 114, whereby withdraw of the plunger of syringe 114 applies a vacuum pressure that draws the first drug from source 122 into the barrel of syringe 114. When a sufficient volume of first drug has been transferred into the primary syringe 114, the system can be adjusted to the configuration of FIG. 2D, which shows a second stage of providing the volume of first drug to reservoir 128. In particular, valves 112, 116, and 118 are adjusted such that only first blood reservoir 128 is fluidically connected to primary syringe 114, whereby depressing the plunger of syringe 114 applies a positive pressure that pushes the first drug from the syringe barrel into the first blood reservoir 128.

Figure 2E:
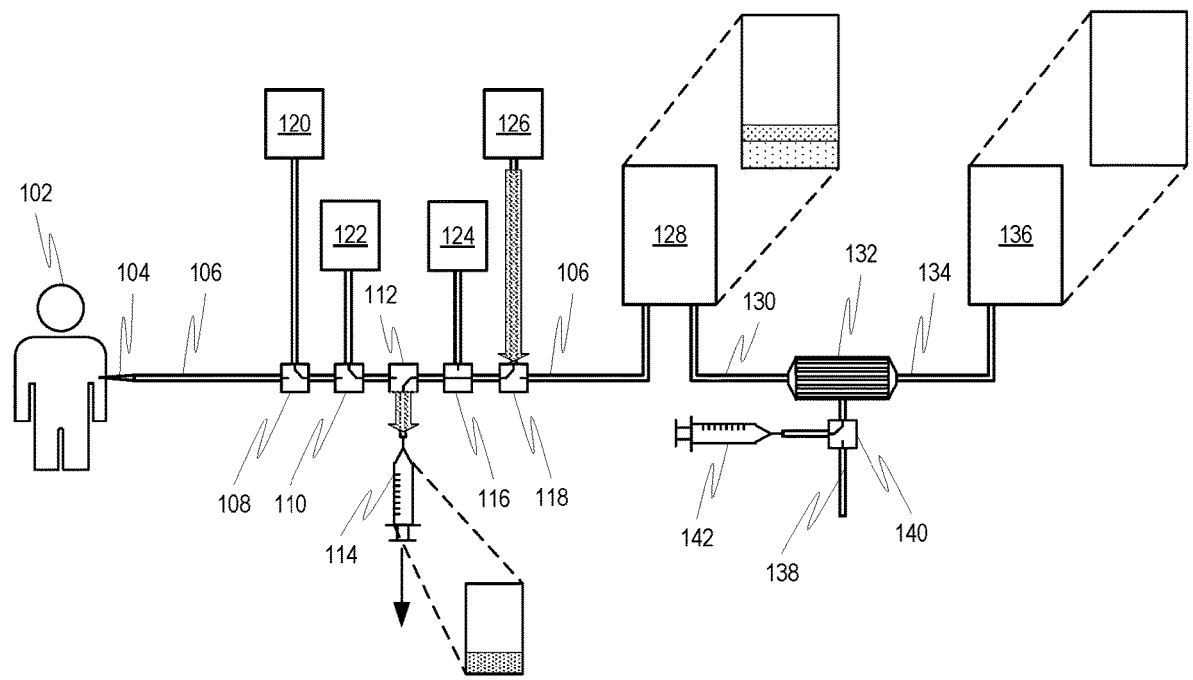
Figure 2F:
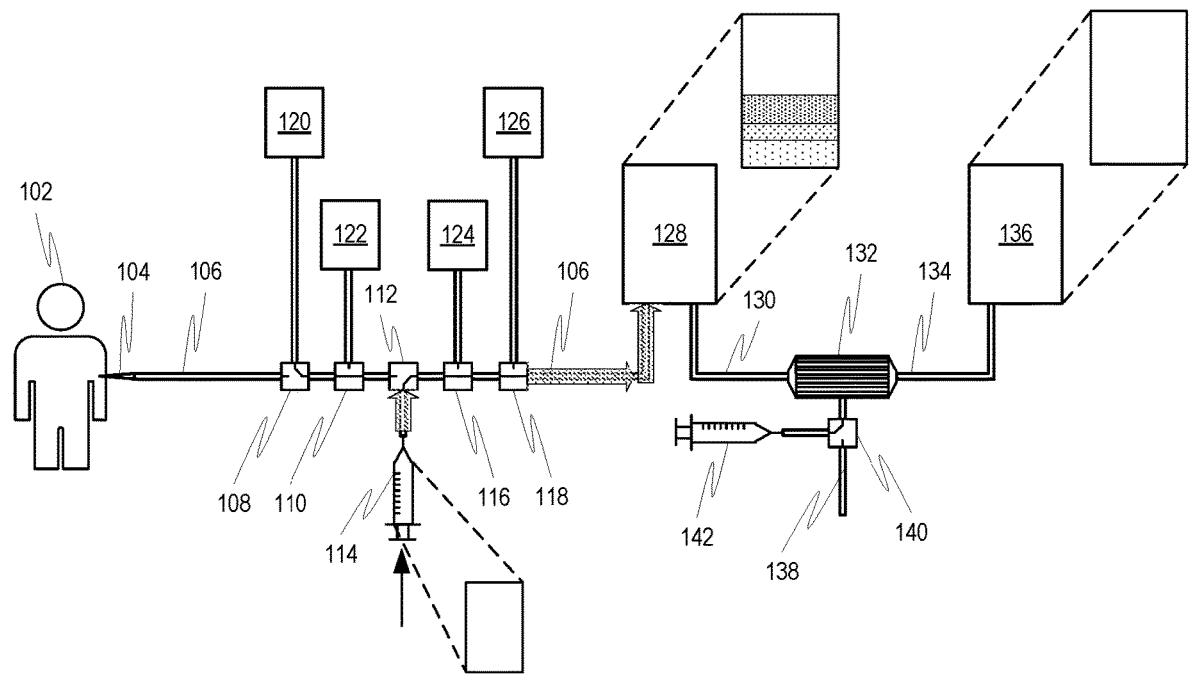

After the first drug, a volume of second fluid can be added. For example, FIG. 2E shows a first stage of providing a volume of second fluid from source 126 to reservoir 128. In particular, valves 112, 116, and 118 are adjusted such that only source 126 is fluidically connected to primary syringe 114, whereby withdraw of the plunger of syringe 114 applies a vacuum pressure that draws the second fluid from source 126 into the barrel of syringe 114. When a sufficient volume of second fluid has been transferred into the primary syringe 114, the system can be adjusted to the configuration of FIG. 2F, which shows a second stage of providing the volume of second fluid to reservoir 128. In particular, valve 118 is adjusted such that only first blood reservoir 128 is fluidically connected to primary syringe 114, whereby depressing the plunger of syringe 114 applies a positive pressure that pushes second fluid from the syringe barrel into the first blood reservoir 128. For example, while not ideal, a combination of 1-liter D5/NS as source 120 and 4-liters Hartmann's solution (i.e., lactated ringers) as source 126 can be used to make an adequate hemofiltration solution to manage uremia, acidemia, and hyperkalemia.

Figure 2G:
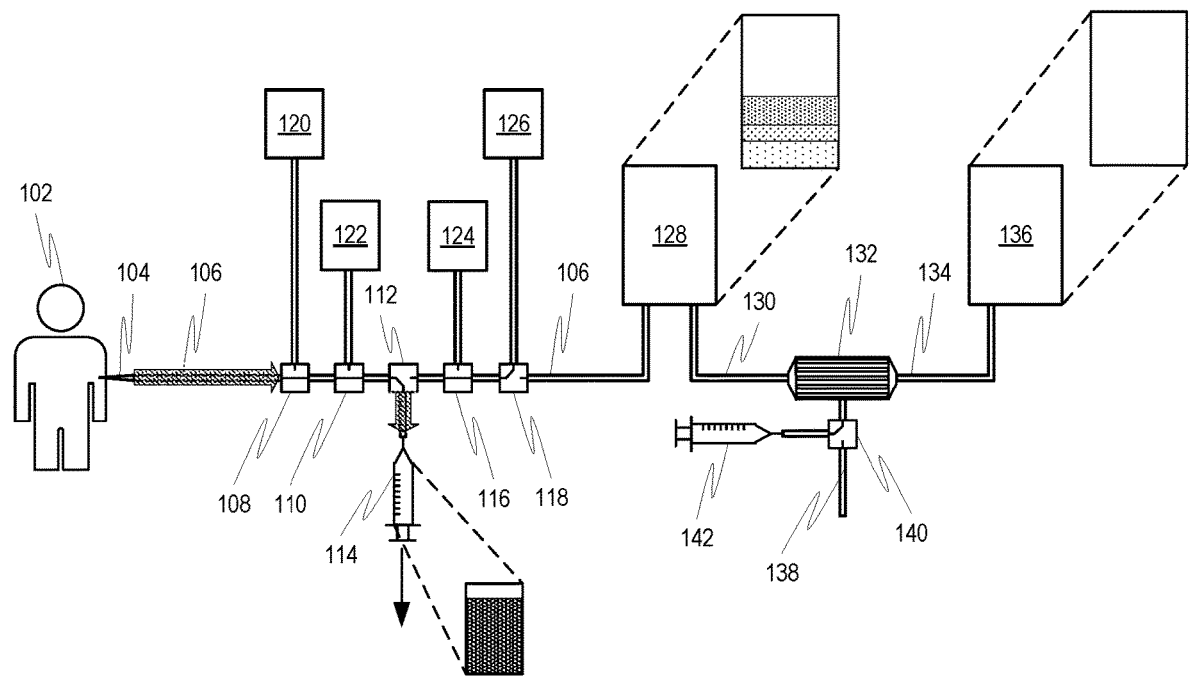
Figure 2H:
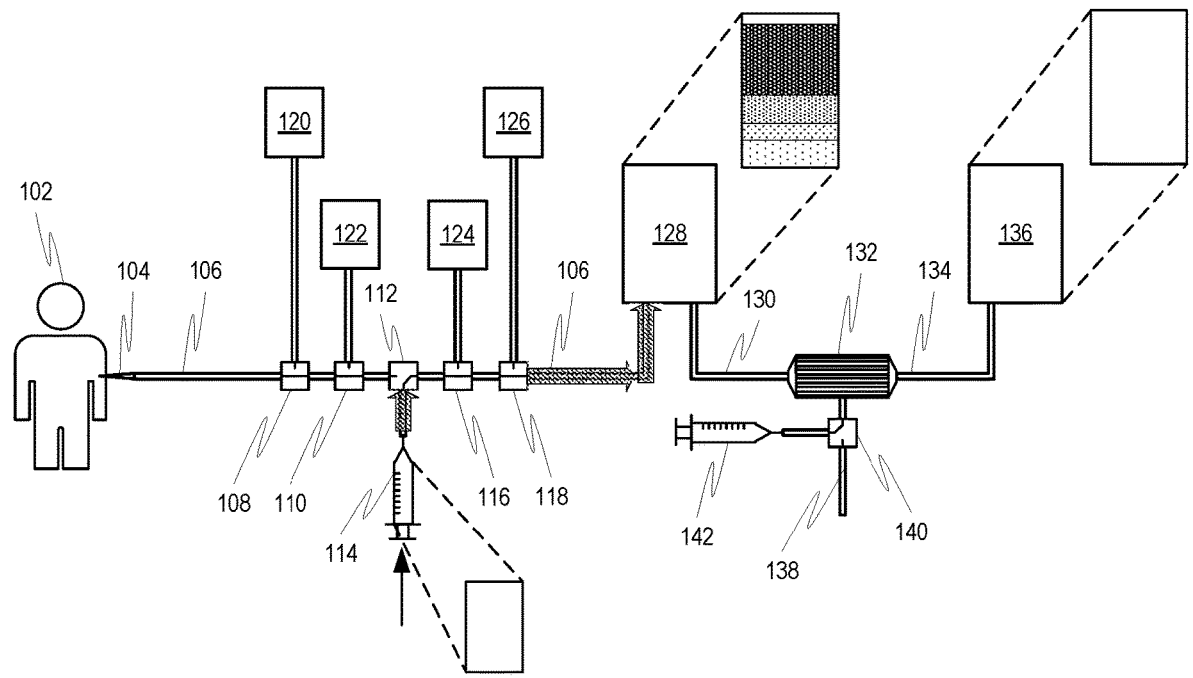

After the second fluid, a volume of blood from the patient 102 can be added. For example, FIG. 2G shows a first stage of providing a volume of blood from patient 102 to reservoir 128. In particular, valves 108, 110, and 112 are adjusted such that only vascular access 104 is fluidically connected to primary syringe 114, whereby withdraw of the plunger of syringe 114 applies a vacuum pressure that draws blood from the patient 102 into the barrel of syringe 114. When a sufficient volume of blood has been transferred into the primary syringe 114, the system can be adjusted to the configuration of FIG. 2H, which shows a second stage of providing the volume of blood to reservoir 128. In particular, valves 112, 116, and 118 are adjusted such that only first blood reservoir 128 is fluidically connected to primary syringe 114, whereby depressing the plunger of syringe 114 applies a positive pressure that pushes blood from the syringe barrel into the first blood reservoir 128.

Figure 2I:
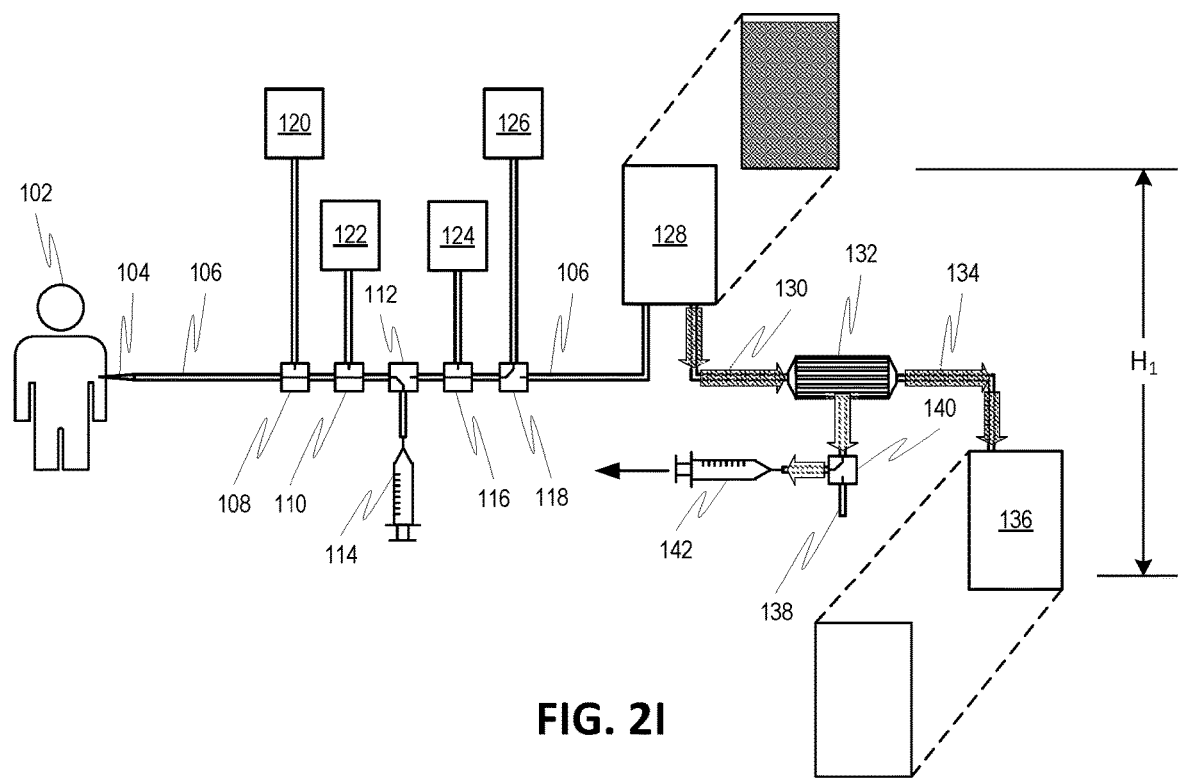

Note that FIGS. 2B-2H show fluid volumes in blood reservoir as being a lamination of volumes for illustration and discussion purposes only. In practical implementations, the first fluid, first drug, second fluid, and blood would all mix together within reservoir 128 to provide a single mixed volume, for example, as illustrated in FIG. 2I.

Once the blood has been added to reservoir 128, blood treatment processing can be effected by flowing blood through the filtration device 132. For example, FIG. 2I shows a first stage of blood treatment processing. In particular, valve 118 is adjusted to isolate blood reservoir 128 from the remainder of conduit 106. Blood flow from the first reservoir 128 through filtration device 132 to the second reservoir 136 is achieved by providing a relative height difference ($H_1$) between the reservoirs 128, 136, for example, by moving the first reservoir 128 above the second reservoir 136, by moving the second reservoir 136 below the first reservoir 128, or by a combination of moving the first reservoir 128 up and the second reservoir 136 down. Valve 140 is adjusted such that the outlet port of the filtration device 132 and secondary syringe 142 are fluidically connected, whereby withdraw of the plunger of syringe 142 applies a vacuum pressure that draws effluent across a membrane from the flowing blood.

Figure 2J:
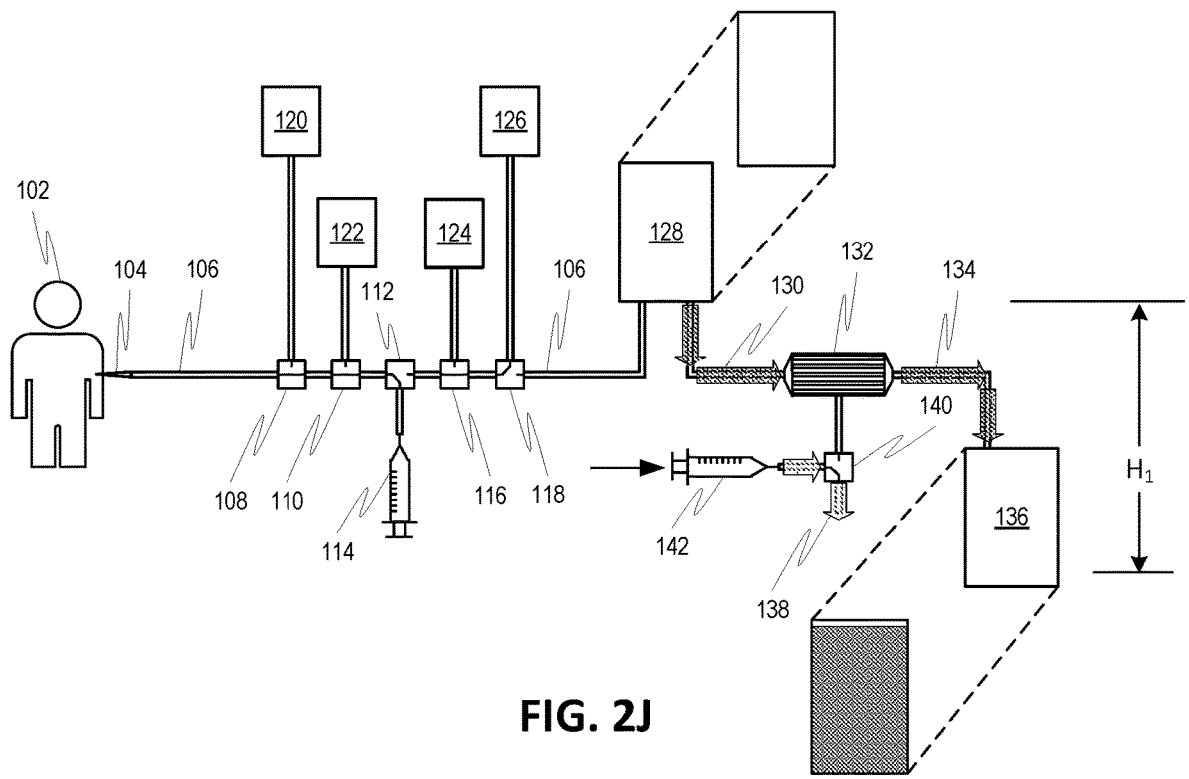

When all of the blood has been transferred from reservoir 128 to reservoir 136 and/or when a barrel of syringe 142 has been filled with effluent, the system can be adjusted to the configuration of FIG. 2J, which shows a second stage of blood treatment processing. In particular, valve 140 can be adjusted such that secondary syringe 142 is connected to an outlet end of drain line 138, whereby depressing the plunger of syringe 142 applies a positive pressure that pushes the effluent from the syringe barrel for waste (e.g., to a waste container, drain, or other medical disposal).

Figure 2K:
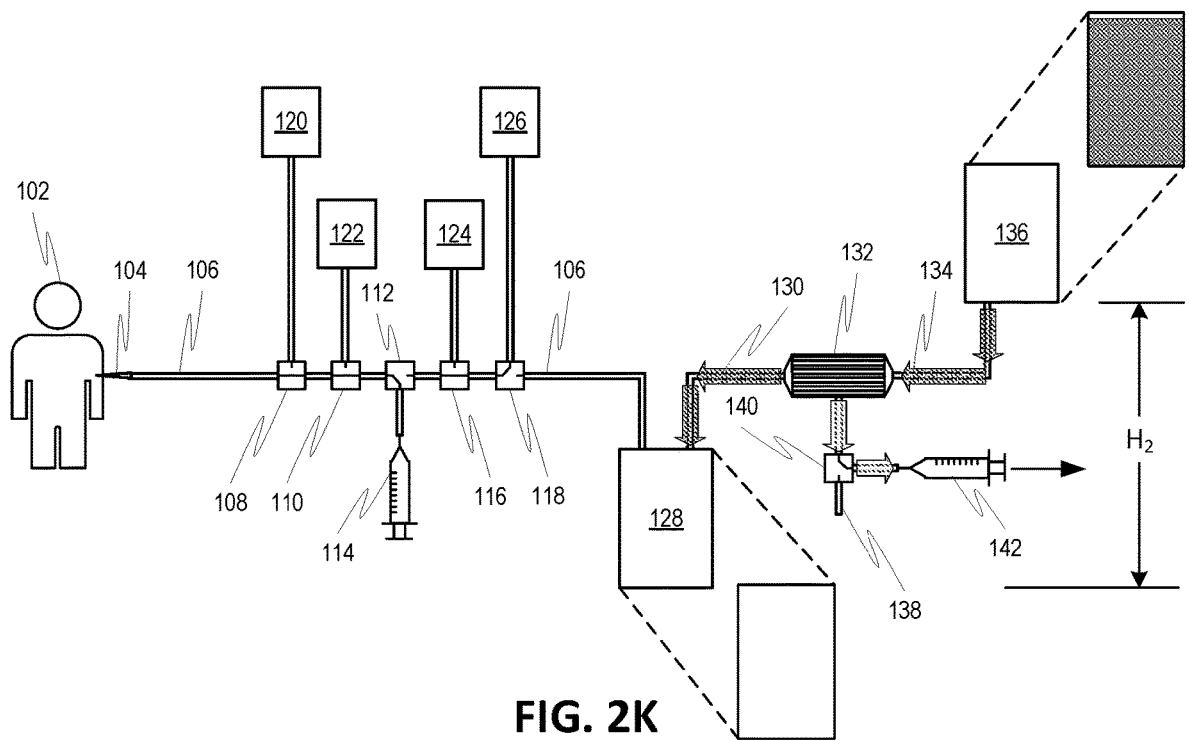

After FIG. 2J, the system can be adjusted to the configuration of FIG. 2K, which shows a third stage of blood treatment processing. Blood flow from the second reservoir 136 back through filtration device 132 to the first reservoir 128 is achieved by reversing the relative height difference ($H_2$) between the reservoirs 128, 136, for example, by moving the first reservoir 128 below the second reservoir 136, by moving the second reservoir 136 above the first reservoir 128, or by a combination of moving the first reservoir 128 down and the second reservoir 136 up. Valve 140 is adjusted such that the outlet port of the filtration device 132 and secondary syringe 142 are again fluidically connected, whereby withdraw of the plunger of syringe 142 applies a vacuum pressure that again draws effluent across a membrane from the flowing blood.

Figure 2L:
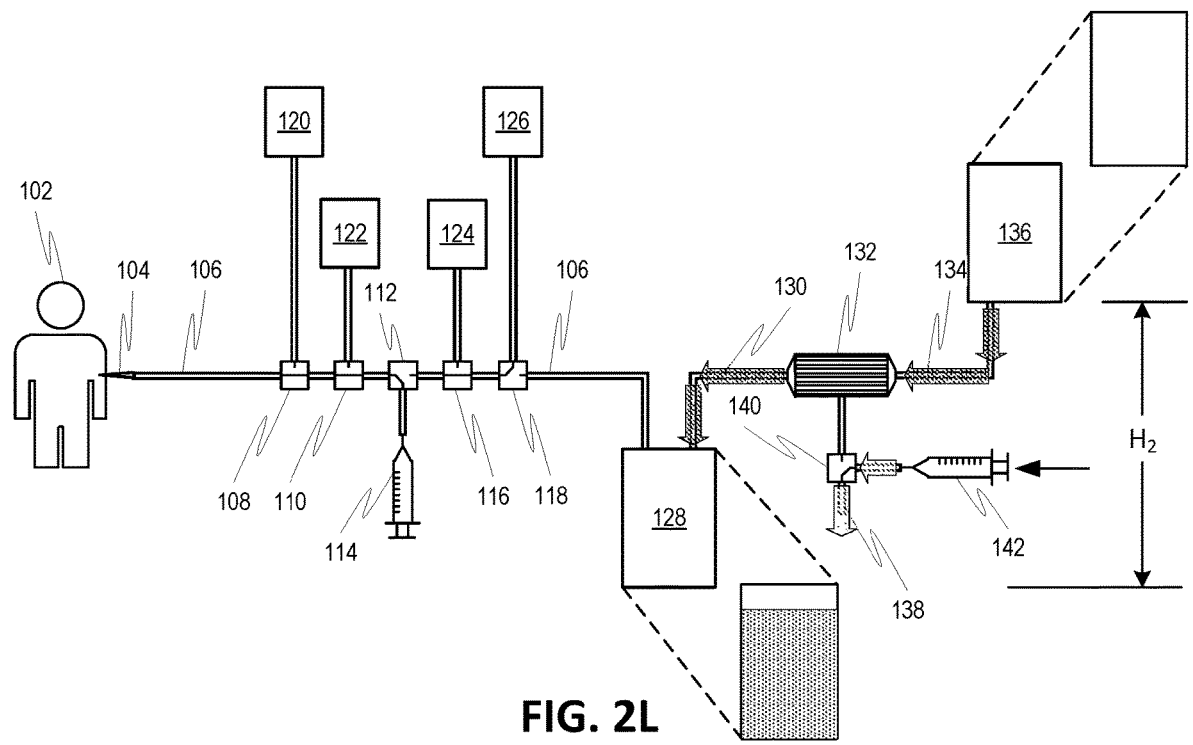

When all of the blood has been transferred from reservoir 136 to reservoir 128 and/or when a barrel of syringe 142 has been filled with effluent, the system can be adjusted to the configuration of FIG. 2L, which shows a fourth stage of blood treatment processing. In particular, valve 140 can be adjusted such that secondary syringe 142 is connected to an outlet end of drain line 138, whereby depressing the plunger of syringe 142 applies a positive pressure that pushes the effluent from the syringe barrel for waste (e.g., to a waste container, drain, or other medical disposal). Thus, other than the relative heights of reservoirs 128, 136, the second stage of FIG. 2J and the fourth stage of FIG. 2L may be substantially similar.

Figure 2M:
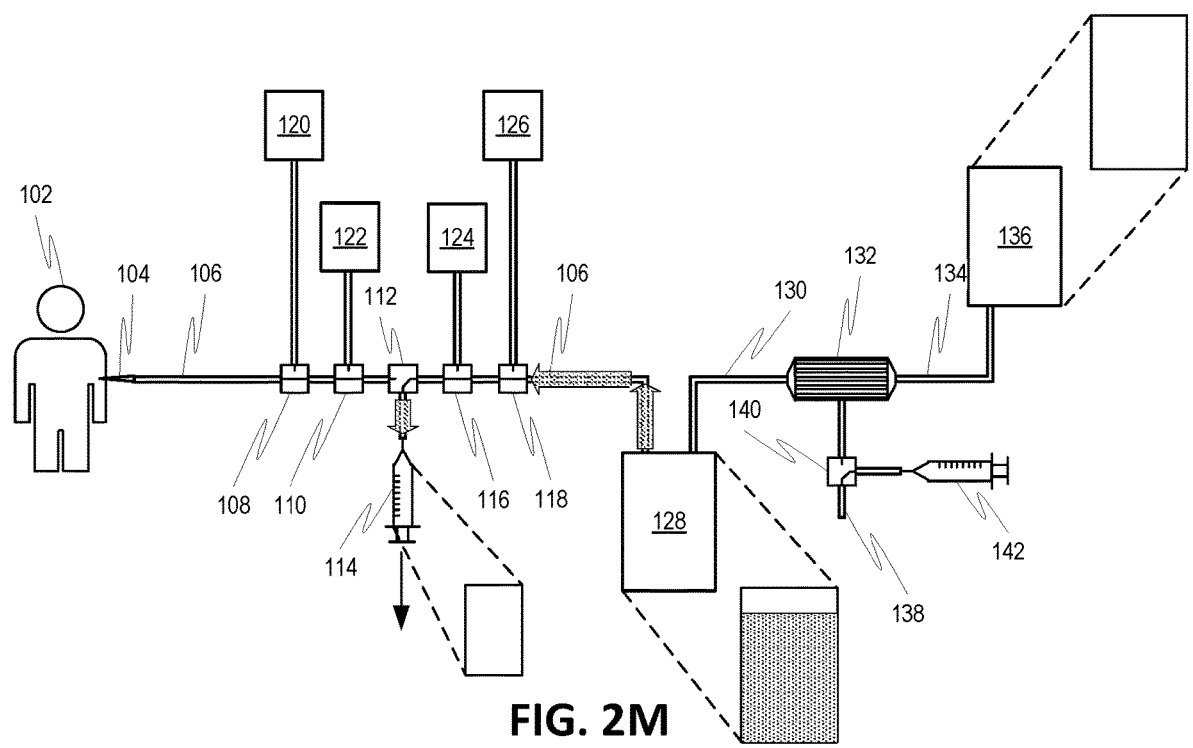
Figure 2N:
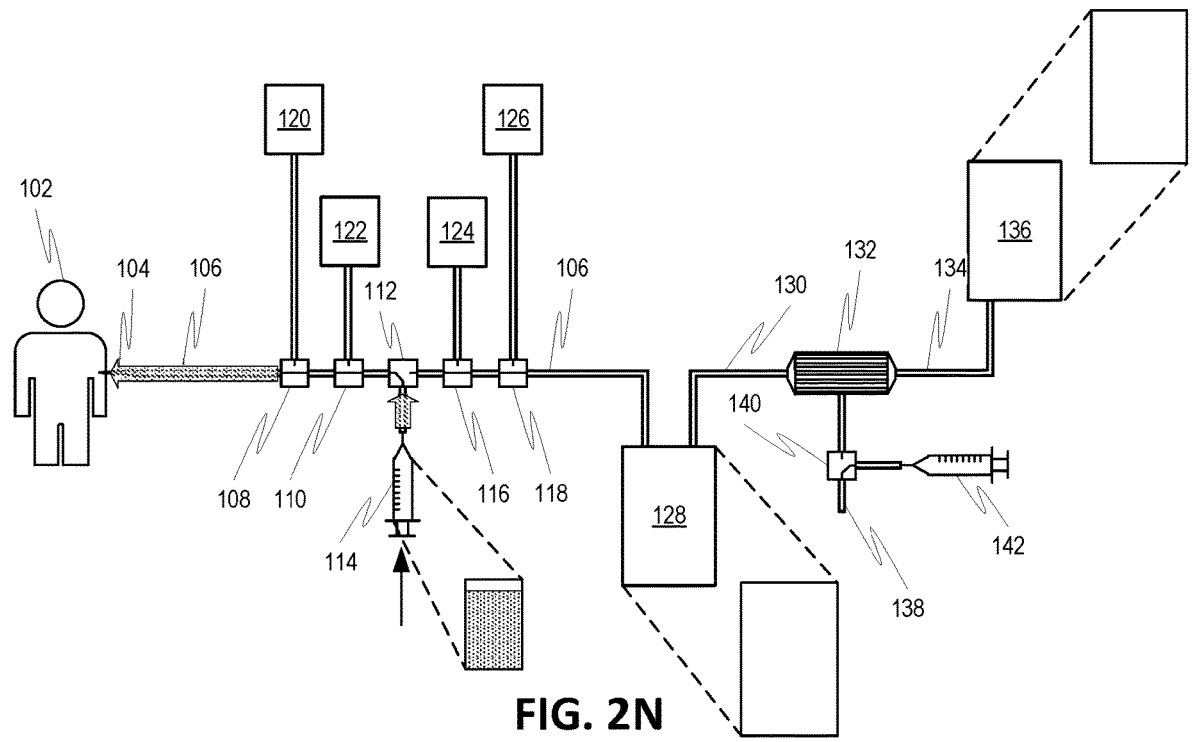

The process of FIGS. 2I-2K can be repeated numerous times in an iterative fashion, on the same batch of blood or body fluid, for example, until sufficient effluent is removed by filtration device. After treatment processing and once the volume of treated blood is in the first reservoir 128, the volume of blood can be returned to the patient 102. For example, FIG. 2M shows a first stage of returning the treated blood to patient 102. In particular, valves 112, 116, and 118 are adjusted such that only first reservoir 128 is fluidically connected to primary syringe 114, whereby withdraw of the plunger of syringe 114 applies a vacuum pressure that draws blood from the reservoir 128 into the barrel of syringe 114. When a sufficient volume of blood has been transferred into the primary syringe 114, the system can be adjusted to the configuration of FIG. 2N, which shows a second stage of returning the treated blood to patient 102. In particular, valves 108, 110, and 112 are adjusted such that only vascular access 104 is fluidically connected to primary syringe 114, whereby depressing the plunger of syringe 114 applies a positive pressure that pushes blood from the barrel of syringe 114 into the patient 102.

Figure 2O:
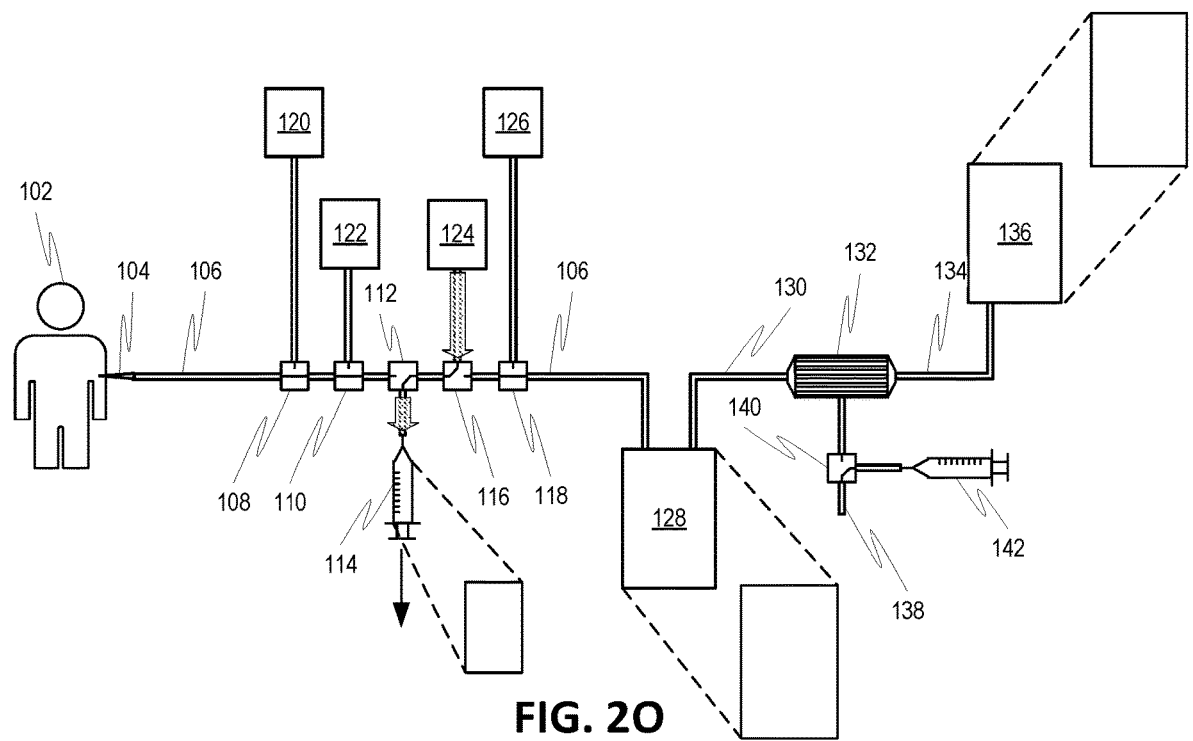
Figure 2P:
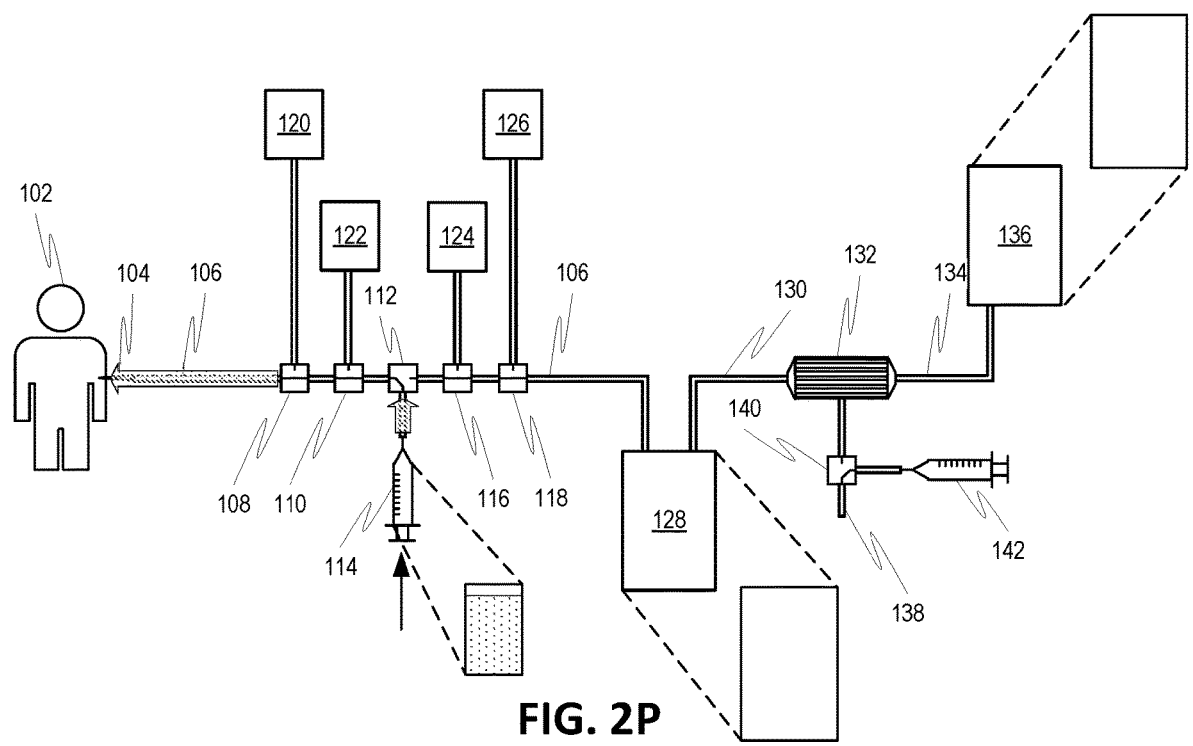

After return of the treated blood, a volume of second drug can be added. For example, FIG. 2O shows a first stage of providing a volume of second drug from source 124 to patient. In particular, valves 112, 116 are adjusted such that only source 124 is fluidically connected to primary syringe 114, whereby withdraw of the plunger of syringe 114 applies a vacuum pressure that draws the second drug from source 124 into the barrel of syringe 114. When a sufficient volume of second drug has been transferred into the primary syringe 114, the system can be adjusted to the configuration of FIG. 2P, which shows a second stage of providing the volume of second drug to patient 102. In particular, valves 108, 110, and 112 are adjusted such that only vascular access 104 is fluidically connected to primary syringe 114, whereby depressing the plunger of syringe 114 applies a positive pressure that pushes the second drug from the syringe barrel into the patient 102.

Note that extracorporeal treatments other than the hemofiltration specifically discussed above are also possible according to one or more contemplated embodiments, by appropriate modification of the filtration device 132 and control of fluid flows provided by the primary and secondary syringes 114, 142 and height differences of the blood reservoirs 128, 136. Moreover, fluid flows other than those specifically described above are also possible according to one or more contemplated embodiments. For example, fluid from either or both of sources 120, 126 can be infused into patient 102 by appropriate control of valves 108, 110, 112, 116, and 118 and primary syringe 114, in a manner similar to that discussed above.

In some embodiments, the methods and systems disclosed can be used to process other body fluids. For example, accumulation of fluid in the abdominal cavity is called ascites. Ascites can be common with patients with cirrhosis, liver disease or congestive heart failure. When removing a body fluid such as ascites, a diuretic can also be administered. Commonly used diuretics include spironolactone (Aldactone) and/or furosemide (Lasix). When fluid accumulation cannot be treated optimally with diuretics and a salt restricted diet, patients may require a large amount of fluid be removed (paracentesis) for relief of symptoms. The disclosure includes methods and systems for treating ascites, by the withdrawal of ascites. Optionally, the withdrawn ascitic fluid can be concentrated and reinfused.

Paracentesis is carried out under strict sterile conditions. Ascites is withdrawn from patient 102 via access 104 and conveyed to reservoir 128 for temporary storage until treatment processing. Syringe 114 can be used to remove the ascitic fluid. Alternatively, ascitic fluid removal may use gravity. The needle is usually inserted into the left or right lower abdomen, where the needle is advanced through the subcutaneous tissue and then through the peritoneal cavity. In certain aspects, the ascitic fluid is drained in a single session, assisted by gentle mobilization of the cannula or turning patient 102 if necessary.

The body fluid (e.g., ascites) from reservoir 128 is conveyed to filtration device 132, where the ascites is subjected to a treatment process such as concentration and is thereafter returned to the reservoir 128. The concentrated ascites (e.g., a protein rich concentrate) can be returned to patent 102 via conduit 106. Albumin may also be infused in lieu of the concentrated ascites, or in addition to the concentrated ascites.

In certain instances, the filter can be for example, an extracorporeal hemoadsorption filter device to remove cytokines from circulating blood such as a biocompatible, sorbent bead technology e.g., CytoSorb™, CytoSorbents™, Inc., CytoSorb hemoadsorption beads are polystyrene-divinylbenzene porous particles (450 μm avg. particle diameter, 0.8-5 nm pore diameter, 850 $m^2/g$ surface area) with a biocompatible polyvinyl-pyrrolidone coating. See for example, U.S. Pat. No. 8,647,666 which claims a method of using a composition comprising polystyrene divinyl benzene copolymer and a polyvinyl pyrrolidone polymer.

In certain other instances, the filter is Seraph® Microbind® Affinity Blood Filter, which is a filter that allows body fluids to pass over microbeads coated with molecular receptor sites that mimic the receptors on human cells which pathogens use to colonize when they invade the body. The adsorption media is a flexible platform that uses covalently-bonded, immobilized heparin or heparan sulfate for its unique binding capacity. See, for example, U.S. Pat. No. 8,758,286 or 9,173,989, disclosing at least one polysaccharide adsorbent, or immobilized heparin.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

It is thus apparent that there is provided, in accordance with the present disclosure, syringe-based manual extracorporeal blood treatment systems and methods employing batch processing. Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

What is claimed is:

1. A manual blood treatment system comprising:
first and second reservoirs for holding a batch of blood from a patient;
a first conduit for conveying blood from a vascular access of the patient during a first stage and for returning treated blood to the vascular access during a third stage, the first conduit having only a single lumen;
a filter for performing, during a second stage, an extracorporeal treatment on blood passing therethrough by removing waste molecules and/or fluid; and
a first syringe coupled to the first conduit via a first valve between the vascular access and the first reservoir,
wherein fluid ports of the first and second reservoirs are connected to each other by a flow path through the filter such that the batch of blood can flow between the first and second reservoirs via the filter,
the first reservoir is constructed to be displaced vertically relative to the second reservoir and vice versa, such that a height difference between the first and second reservoirs causes blood to flow between the reservoirs due to gravity; and
a second syringe coupled to a drain line from the filter via a second valve,
wherein the second syringe is configured to:
apply a vacuum pressure to the filter when the second valve is in a first orientation, and
apply a positive pressure to push effluent received from the filter along the drain line for disposal when the second valve is in a second orientation.

2. The system of claim 1, wherein the first syringe is configured to:
apply a vacuum pressure to the vascular access when the first valve is in a first orientation to withdraw a volume of blood from the patient via the first conduit, and
apply a positive pressure when the first valve is in a second orientation to push the withdrawn volume of blood along the first conduit to the first reservoir.

3. The system of claim 1, wherein the filter is constructed to provide a hemodialysis, hemofiltration, hemodiafiltration, or hemoperfusion treatment to the blood flowing along the flow path through the filter.

4. The system of claim 1, further comprising:
one or more additional valves disposed along the first conduit between the vascular access and the first valve or between the first valve and the first reservoir,
wherein the first syringe is further configured to:
apply a vacuum pressure to a source of secondary fluid or drug connected to the one or more additional valves when the first valve is in the first orientation to withdraw a volume of secondary fluid or drug, and
apply a positive pressure when the first valve is in the second orientation to push the withdrawn volume of secondary fluid or drug along the first conduit to the first reservoir.

5. The system of claim 4, wherein the secondary fluid or drug comprises at least one of replacement fluid, flushing fluid, intravenous fluid, anticoagulant, or anticoagulant reversal agent.

6. A manual blood treatment method comprising:
(a) using a first syringe coupled to a first conduit by a first valve in a first orientation, applying a vacuum to a vascular access of a patient to withdraw a first volume of blood from a patient;
(b) switching the first valve to a second orientation;
(c) with the first valve in the second orientation, applying a positive pressure using the first syringe to convey the first volume of blood to a first reservoir;
(d) changing respective heights of the first reservoir and a second reservoir, such that the first reservoir is higher than the second reservoir and such that blood in the first reservoir is conveyed to the second reservoir via a flowpath through a filter;
(e) after (d), changing respective heights of the first and second reservoirs such that the second reservoir is higher than the first reservoir and such that blood in the second reservoir is returned to the first reservoir via the flowpath through the filter;
(f) with the first valve in the second orientation, applying a vacuum using the first syringe to withdraw a second volume of blood from the first reservoir;
(g) switching the first valve to the first orientation;
(h) with the first valve in the first orientation, applying a positive pressure using the first syringe to convey the second volume of blood into the patient via the vascular access; and
(i) during (d) and/or (e), using a second syringe coupled to a drain line of the filter by a second valve in a first orientation, applying a vacuum to the filter to withdraw effluent therefrom.

7. The method of claim 6, further comprising:
switching the second valve to a second orientation and applying a positive pressure using the second syringe to convey the withdrawn effluent along the drain line away from the filter for disposal.

8. The method of claim 6, wherein (d) and (e) are repeated more than once to filter the same blood multiple times before proceeding to (f).

9. The method of claim 6, wherein (d) and (e) are effective to perform a hemodialysis, hemofiltration, hemodiafiltration, or hemoperfusion treatment on the blood flowing along the flow path through the filter.

10. The method of claim 6, wherein the second volume of blood is less than the first volume of blood.

11. The method of claim 6, further comprising at least one of:
(S1) infusing a secondary fluid or drug to the first reservoir by:

(S1a) switching the first valve to the first orientation and a third valve, which couples a secondary fluid/drug source to the first conduit, to a first orientation;

(S1b) applying a vacuum to the first conduit to draw a volume of the secondary fluid or drug from the secondary fluid/drug source;

(S1c) switching the first valve to the second orientation; and (S1d) with the first valve in the second orientation, applying a positive pressure using the first syringe to convey the volume of secondary fluid or drug to the first reservoir.

12. The method of claim 7, further comprising at least one of:

(S2) infusing another secondary fluid or drug to the patient by:

(S2a) switching the first valve to the second orientation and a fourth valve, which couples another secondary fluid/drug source to the first conduit, to a first orientation;

(S2b) applying a vacuum to the first conduit to draw a volume of the another secondary fluid or drug from the another secondary fluid/drug source;

(S1c) switching the first valve to the first orientation; and (S1d) with the first valve in the first orientation, applying a positive pressure using the first syringe to convey the volume of the another secondary fluid or drug to the patient via the vascular access.

* * * * *